US00PP14923P3

(12) United States Plant Patent
Bourne

(10) Patent No.: US PP14,923 P2
(45) Date of Patent: Jun. 22, 2004

(54) GRAPEVINE PLANT NAMED '14-44-248'

(50) Latin Name: *Vitis vinifera*
Varietal Denomination: 14-44-248

(75) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 33 days.

(21) Appl. No.: 10/280,573

(22) Filed: Oct. 24, 2002

(65) Prior Publication Data

US 2004/0083511 P1 Apr. 29, 2004

(51) Int. Cl.[7] ..... A01H 5/00

(52) U.S. Cl. ..... Plt./205

(58) Field of Search ..... Plt./205

*Primary Examiner*—Kent Bell
(74) *Attorney, Agent, or Firm*—Jondle & Associates PC

(57) ABSTRACT

This new grape plant named '14-44-248' is new and different because of its very large berry size, elongate berry and very firm, crisp texture. Fruit of the new variety ripens in mid-season producing a very sweet berry which is suitable for the domestic and foreign grape markets.

2 Drawing Sheets

Genus and species: *Vitis vinifera.*

BACKGROUND AND SUMMARY OF THE INVENTION

The new grape plant named '14-44-248' is of *Vitis vinifera* parentage. It resulted from an effort to provide an alternative to 'Redglobe' (U.S. Plant Pat. No. 4,787) in the mid-season, seeded table grape market. Ripening of '14-44-248' is in the same period as 'Thompson Seedless' (unpatented), achieving a sugar level of about 18 degrees brix in the second week of August. Fruit of the new variety hangs well on the vine and sugar levels continue to increase until the third week of September in the Delano, Calif. area. Pedicels of '14-44-248' are very slender and are prone to drying if held in cold storage for long periods of time.

The female parent (unnamed) resulted from a series of crosses involving 'Hunisa', 'Flame Seedless', 'Emperor', and 'Thompson Seedless' (all unpatented). The male parent of the cross is 'Fantasy Seedless' (unpatented). The hybridization resulting in '14-44-248' was made near McFarland, Calif. in 1993. Resulting seeds were stratified and sown in a greenhouse in January of 1994. Seedlings were transplanted to a field in the Delano, Calif. area in March of that same year. The original seedling vine of '14-44-248' was selected from a population of 127 seedlings of like parentage in 1996. it was then propagated by cuttings and grafting to 'Freedom' (unpatented) rootstock near McFarland, Calif. Those resulting plants were stable and typical of the original vine. Subsequent propagations of the variety have also proven stable with true to type plants.

COMPARISON WITH PARENTAL CULTIVAR

The new grape plant named '14-44-248' somewhat resembles the cultivar 'Emperor', from which it descends, but differs by having a much larger berry with crisper texture than fruit of 'Emperor'. It differs from its female parent (unnamed) by having berries with dark red berries rather than white berries. It shares some characteristics with its male parent 'Fantasy Seedless', but differs by having a greater fruitfulness than 'Fantasy Seedless', allowing spur pruning of the vines. Berries of '14-44-248' have sclerified seeds, unlike 'Fantasy Seedless'. Vigor of the new variety is reduced compared to that of 'Fantasy Seedless'.

DESCRIPTION OF THE FIGURES

The accompanying drawings illustrate the following.

DETAILED BOTANICAL DESCRIPTION OF THE INVENTION

Figure 1:
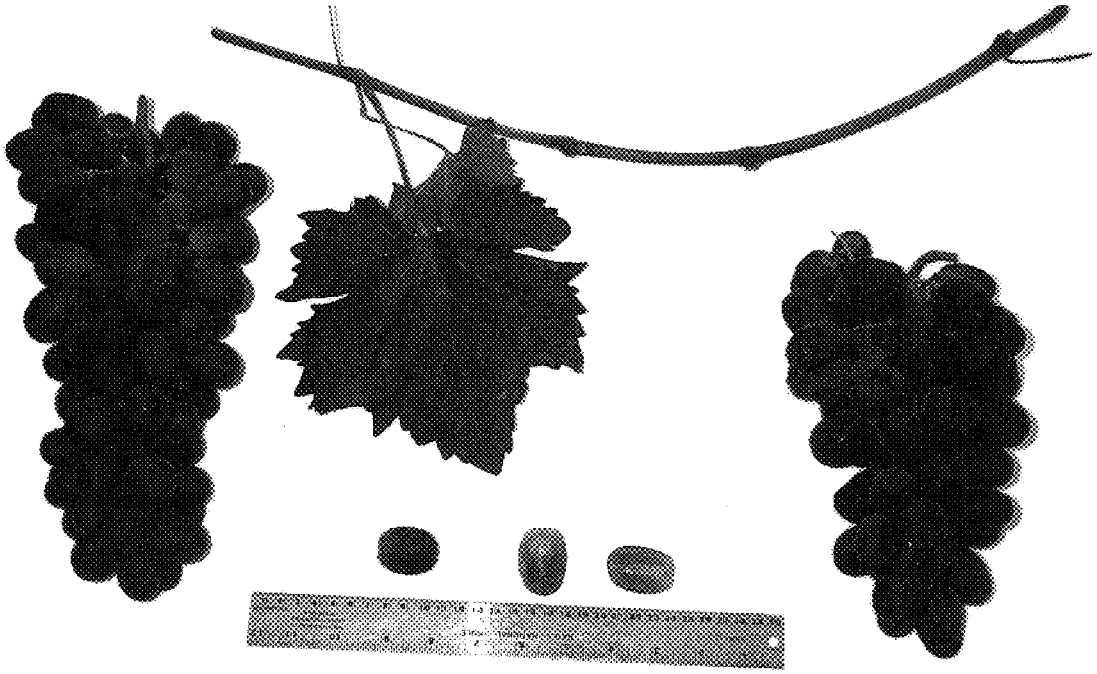
FIG. 1 shows a cane, leaf, natural fruit cluster (left) and fruit cluster following tipping (right).
Figure 2:
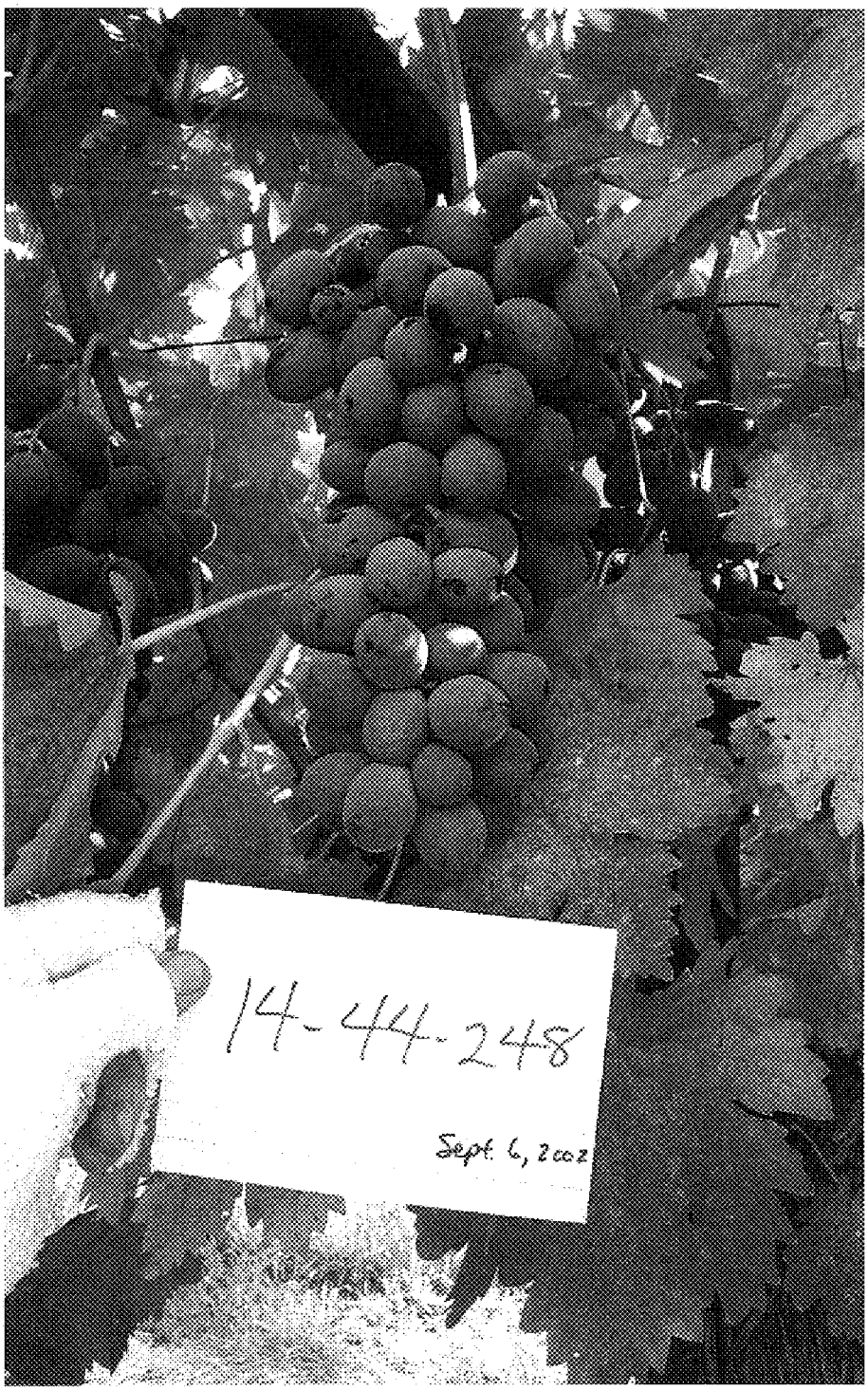
FIG. 2 shows a fruit cluster at harvest.

The following description of grapevine '14-44-248' contains references to color names taken from the Munsell Color Chart for Plant Tissues, published by Munsell Color, New Windsor, N.Y. Descriptors used herein conform to those set forth by the International Board for Plant Genetic Resources Institute Grape Descriptors (Vitis spp.) of 1983 and/or 1997 which were developed in collaboration with the Office International de la Vigne et du Vin (OIV) and the International Union for the Protection of New Varieties of Plants (UPOV) and published in Descriptors for Grapevine (Vitis spp.) (Anonymous, International Plant Genetic Resources Institute, 1997, ISBN 92-9043-352-3).

Descriptions of the new invention apply to vines of '14-44-248' grown on 'Freedom' rootstock at a density of 1,537 vines per hectare grown in Kern County, Calif. in 2001. These vines were in their third year of full production having been planted in 1997. These descriptions are believed to apply generally to the new variety grown under similar circumstances elsewhere:

VINE

General:

*Vigor.*—High, canes average 348 cm. of growth when spur pruned and thinned to 32 shoots per vine on 6 year old vines.

*Density of foliage.*—Dense.
*Productivity.*—Very productive when spur pruned, up to 49,470 kg./hectare.
*Hardiness.*—Observed hardiness to 0 C.
*Rootstock.*—Freedom.

LEAVES

Mature leaves:
*Average blade length.*—17.1 cm.
*Average blade width.*—20.7 cm.
*Size of blade.*—Large.
*Shape.*—Pentagonal.
*Anthocyanin coloration of main veins on the upper side of the blade.*—Present at base of veins, 5R 5/10.
*Mature leaf profile.*—Undulating.
*Blistering surface of blade upper surface.*—Absent.
*Leaf blade tip.*—Curved upward.
*Margins.*—Cleft, serrate, undulating.
*Apex.*—Acuminate.
*Base.*—Sagittate.
*Thickness.*—Medium.
*Undulation of blade between main and lateral veins.*—Strong.
*Shape of teeth.*—Conical, both sides convex.
*Length of teeth.*—5–13 mm.
*Ratio length/width of teeth.*—About 1:1.
*General shape of petiole sinus.*—Open (ovate).
*Tooth at petiole sinus.*—Absent.
*Petiole sinus limited by veins.*—Absent.
*Shape of upper lateral sinus.*—Closed.
*Prostrate hairs between veins on lower surface of blade.*—Absent.
*Erect hairs between hairs on lower surface of blade.*—Absent.
*Prostrate hairs on main veins on lower surface of blade.*—Absent.
*Density of erect hairs on main veins on lower surface of blade.*—Sparse.
*Prostrate hairs on main veins on upper surface of blade.*—Absent.

Upper surface:
*Summer color.*—7.5 GY 4/4 to 4/6.
*Autumn color.*—5Y 8/8.
*Surface texture.*—Smooth.
*Surface appearance.*—Dull.
*Goffering of blade.*—Absent.

Lower surface:
*Summer color.*—5GY 5/6 to 5/10.
*Autumn color.*—5Y 8/6.
*Anthocyanin coloration of main veins on lower leaf surface.*—Present.
*Glossiness.*—Low.
*Pubescence.*—Absent.
*Surface texture.*—Smooth.
*Surface appearance.*—Dull.

Petiole:
*Length of petiole.*—15.7 cm.
*Diameter.*—3 mm.
*Color.*—Most of petiole 2.5GY 8/6 but with streaks of 5R 5/10 in leaves exposed to the sun.
*Length of petiole compared to middle vein.*—About the same.
*Density of prostrate hairs on petiole.*—Absent.
*Density of erect hairs on petiole.*—Absent.
*Shape of base of petiole sinus.*—Mostly closed, inside outline is ovate.

TENDRILS

*Number.*—Tendrils at all nodes above node 5.
*Length.*—26 cm.
*Diameter.*—3 mm.
*Texture.*—Smooth.
*Color.*—2.5GY 8/10.

WOODY SHOOT

Trunk:
*Trunk circumference.*—22.8 cm. at 1 meter height.
*Shape.*—Medium.
*Straps.*—Long, split.
*Surface texture.*—Shaggy.
*Inner bark color.*—2.5YR 4/6 to 4/8.
*Outer bark color.*—7.5YR 7/2.

Canes:
*Shape.*—Broadly elliptical.
*Internode length.*—About 14.0 cm.
*Width at node.*—About 2.0 cm.
*Cross section.*—Circular.
*Surface.*—Smooth.
*Main color.*—5YR 4/6 to 4/8.
*Lenticels.*—Inconspicuous.
*Erect hairs on nodes.*—Absent.
*Erect hairs on internodes.*—Absent.
*Growth of axillary shoots.*—Prolific.

Laterals:
*Shape.*—Circular to broadly elliptical.
*Number.*—Lateral shoots genrally develop at all nodes above node 2.
*Length.*—35.5–119.4 cm.
*Diameter.*—5–9 mm.
*Internode length.*—3–8 cm.
*Color.*—5YR 5/6.

Buds:
*Shape.*—Conical.
*Length.*—7 mm.
*Width.*—7 mm.
*Height.*—6 mm.
*Color.*—5YR 5-6.
*Cane bud fruitfulness.*—Basal buds fruitful, 1–2 clusters per shoot.

FLOWERS

General:
*FIower sex.*—Perfect.
*Length of first inforescence.*—17.1 cm.
*Position of first flowering nodes.*—$3^{rd}$ or $4^{th}$.
*Number of inflorescences per shoot.*—1 or 2.
*Pedicel length.*—3.5 mm.
*Calyptra color.*—5GY 7/8.
*Ovary length.*—2 mm.
*Ovary width.*—1.5 mm.
*Ovary color.*—5GY 4/8.
*Filament length.*—2 mm.
*Filament color.*—2.5 GY 8/2.
*Anther length.*—1 mm.
*Anther color.*—2.5GY 8/8.
*Date of full bloom.*—May 18, 2001 in McFarland, Calif.

FRUIT

General:
*Ripening period.*—Early; about 1 week after 'Thompson Seedless' at Delano, Calif.

Date of ripening: About Aug. 10, 2001.
*Use.*—Fresh market.
*Keeping quality.*—Good.
*Resistance.*—Insects: typical of *Vitis vinifera*. Diseases: typical of *Vitis vinifera*.
*Shipping quality.*—Good.
*Date of first harvest.*—Aug. 10, 2001.
*Solids-sugar.*—High, about 20 brix at full maturity.
*Refractometer test.*—26.0 brix.

Cluster:
*Bunch size.*—Large.
*Bunch length* (*peduncle excluded*).—About 30 cm.
*Bunch width.*—About 10.5 cm.
*Bunch weight* (*natural*).—1069 g.
*Bunch density.*—Low.
*Number of berries.*—119.
*Form.*—Conical.

Peduncle:
*Length of peduncle.*—4 cm.
*Lignification of peduncle.*—Strong, upper 1 cm.
*Color.*—7.5YR 4/4.

Berry:
*Size.*—Large.
*Uniformity of size.*—Variable.
*Berry weight* (*natural*).—12.8 g.
*Shape.*—Elliptic.
*Presence of seeds.*—Yes, avg. wt.=48 mg.
*Cross section.*—Circular.
*Dimensions.*—Longitudinal axis about 3.2 cm.; horizontal axis about 2.5 cm.
*Skin color* (*without bloom*).—Reddish black, 5RP 3/4 to 3/6.
*Coloration of flesh.*—Translucent, 2.5 GY 8/2.
*Juiciness of flesh.*—Very juicy.
*Berry firmness.*—Very firm.
*Particular flavor.*—Neutral, typical vinifera.
*Bloom* (*cuticular wax*).—Strong.
*Pedicel length.*—10 mm.
*Berry separation from pedicel.*—Moderate.

Skin:
*Thickness.*—Medium.
*Texture.*—Tender.
*Reticulation.*—Absent.
*Roughness.*—Variable, smooth to rough.
*Tenacity.*—Tenacious to flesh.
*Tendency to crack.*—Resistant.

Seeds:
*Number per berry.*—2.75 seeds/berry.
*Seed weight.*—47 mg./seed.
*Seed color.*—7.5 YR 5/4.

What is claimed is:

1. A new and distinct variety of grape plant named '14-44-248' as herein illustrated and described.

* * * * *

MZI Selection 14-44-248